United States Patent [19]

Fischell et al.

[11] Patent Number: 5,295,969

[45] Date of Patent: Mar. 22, 1994

[54] VASCULAR ACCESS DEVICE WITH AIR-TIGHT BLOOD CONTAINMENT CAPABILITY

[75] Inventors: Robert E. Fischell, Dayton, Md.; David R. Fischell, Fair Haven, N.J.; Tim A. Fischell, Los Altos, Calif.

[73] Assignee: Cathco, Inc., Dayton, Md.

[21] Appl. No.: 874,366

[22] Filed: Apr. 27, 1992

[51] Int. Cl.⁵ .................................. A61M 5/178
[52] U.S. Cl. ........................ 604/168; 604/164; 604/167; 604/900
[58] Field of Search ............. 604/158, 164, 167–169, 604/900

[56] References Cited

U.S. PATENT DOCUMENTS

| | | |
|---|---|---|
| 1,100,181 | 6/1914 | Hart . |
| 2,578,814 | 12/0951 | Kollsman . |
| 2,623,520 | 12/1952 | Bamford, Jr. . |
| 2,658,511 | 11/1953 | Furnell . |
| 3,093,134 | 6/1963 | Roehr . |
| 3,454,006 | 7/1969 | Langdon . |
| 3,727,613 | 4/1973 | Sorenson et al. . |
| 3,811,441 | 5/1974 | Sarnoff . |
| 3,859,998 | 1/1975 | Thomas et al. . |
| 4,108,175 | 8/1978 | Orton ............................ 604/168 |
| 4,193,399 | 3/1980 | Robinson . |
| 4,274,408 | 6/1981 | Nimrod . |
| 4,468,224 | 8/1984 | Enzmann et al. . |
| 4,525,157 | 6/1985 | Vaillancourt ..................... 604/52 |
| 4,534,763 | 8/1985 | Gettig et al. . |
| 4,758,225 | 7/1988 | Cox et al. ........................ 604/126 |
| 4,832,696 | 5/1989 | Luther et al. . |
| 4,850,960 | 7/1989 | Grayzel . |
| 4,894,052 | 1/1990 | Crawford ....................... 604/63 |
| 5,032,116 | 7/1991 | Peterson et al. .................. 604/168 |
| 5,045,065 | 9/1991 | Raulerson . |
| 5,137,518 | 8/1992 | Mersch . |
| 5,147,314 | 9/1992 | Vaillancourt ..................... 604/158 |

FOREIGN PATENT DOCUMENTS

| | | |
|---|---|---|
| 681640 | 3/1964 | Canada . |
| 139872 | 5/1985 | European Pat. Off. ............ 604/168 |

*Primary Examiner*—C. Fred Rosenbaum
*Assistant Examiner*—Corrine Maglione
*Attorney, Agent, or Firm*—Morton J. Rosenberg; David I. Klein

[57] ABSTRACT

The present invention is a means for accessing blood vessels for the insertion of a guide wire while preventing the free release of blood. Specifically, a hollow, thin-walled metal tube typically having a sharp point at its distal end is joined at its proximal end to a transparent viewing section. The viewing section has a distal narrow lumen and a proximal chamber which has a cap at its proximal end. The cap encloses a pressure sealing means through which a guide wire can be passed. After the distal end of the metal tube is placed in an artery, blood will rush through the metal tube and into the viewing section. The air in the air-tight proximal chamber will alternatively be compressed between diastolic and systolic blood pressure. Feedback to the operator that the distal end of the metal tube is properly placed within an artery can be achieved by observing the reciprocating pulsatile motion of the blood column within the distal narrow lumen of the viewing section. When the proper pulsatile motion is observed, a guide wire can be passed through the sealing means in the cap, through the viewing section, through the metal tube and finally the guide wire will enter the lumen of the artery.

24 Claims, 4 Drawing Sheets

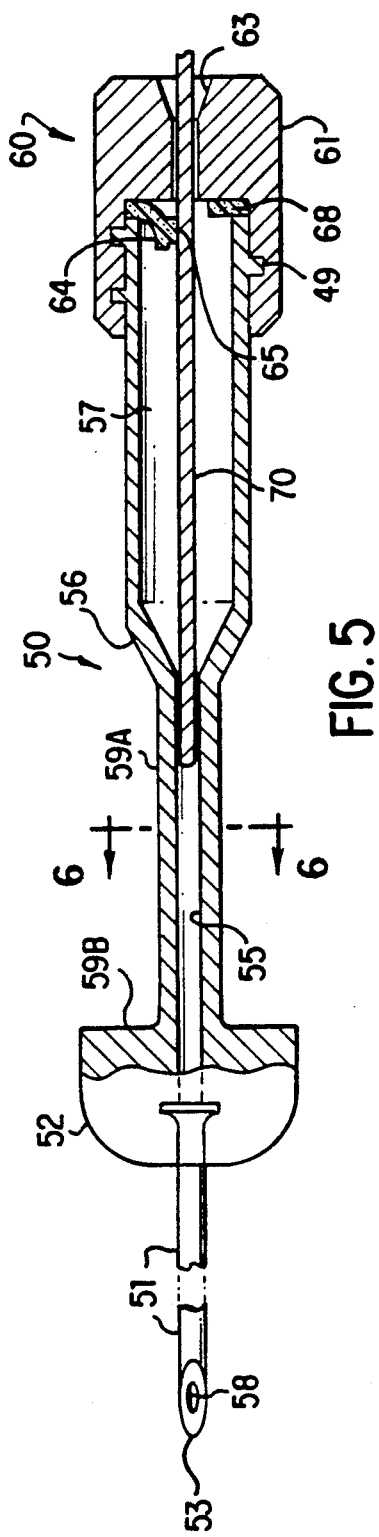
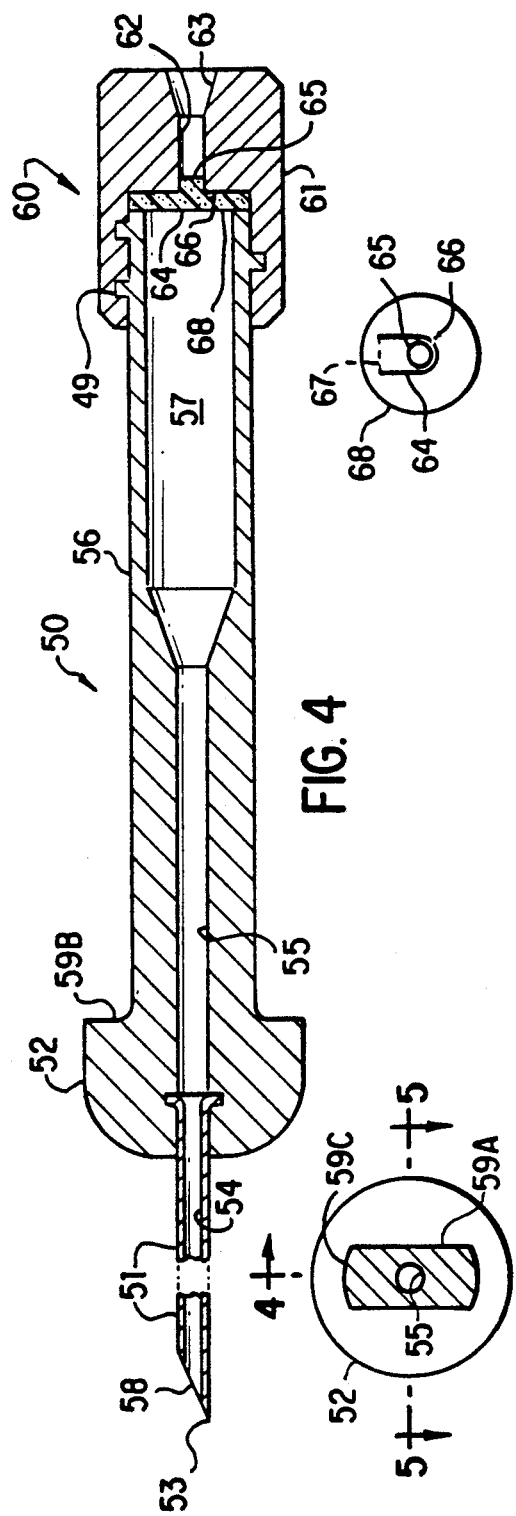
FIG. 5
FIG. 4
FIG. 7
FIG. 6

VASCULAR ACCESS DEVICE WITH AIR-TIGHT BLOOD CONTAINMENT CAPABILITY

FIELD OF USE

This device is in the field of means and methods for accessing human blood vessels for a multiplicity of purposes including the placement of guide wires, introducer sheaths and catheters.

BACKGROUND OF THE INVENTION

Interventional cardiologists and radiologists currently practice a wide range of procedures that require percutaneous access to the human vascular system. In many of these procedures, percutaneous access occurs at the site of the common femoral artery or vein at the groin for the purpose of passing guide wires and introducer sheaths. Catheters can then be advanced through these sheaths to many places within the human vascular system. One method for performing this procedure utilizes a hollow steel cannula with a separate sharpened stylet needle through its center which is pushed through skin and then completely through the common femoral artery. The stylet is then removed and the steel cannula is pulled back slowly until blood under arterial pressure squirts vigorously in a pulsatile manner out of the cannula's proximal end thus indicating that the cannula's distal end is properly placed within the artery. A guide wire is then placed through the cannula and advanced into the artery, and then the cannula is pulled out. A variety of introducer sheaths and/or catheters can then be advanced over the guide wire and into the arterial system.

Another method for accessing arteries is by means of an introducer needle with a sharpened distal end that does not use a stylet needle. This introducer needle is placed through the skin at the groin and advanced until the opening of its sharpened distal end lies within the arterial lumen. When this occurs, blood squirts forcibly in a pulsatile manner out of the needle's proximal end. The pulsatile blood flow indicates that the introducer needle is properly located in the artery so that a guide wire can be inserted through the introducer needle followed by the introducer sheaths and catheters to be used for the procedure.

The blood squirting out of the cannula at arterial pressure results in a considerable release of blood which can find its way into the eyes, nose, or other openings of health care workers in close proximity to the patient.

Besides being messy and causing unnecessary blood loss to the patient, the squirted out blood represents a risk to the health care workers who could be exposed to infectious diseases carried in the patients blood.

SUMMARY OF THE INVENTION

The present invention as described herein overcomes the deficiencies of the prior art arterial access devices by offering a simple, inexpensive, easy to use means and method for inserting guide wires into the femoral artery without allowing the uncontrolled release of arterial blood. Additionally the present invention can be used for placing guide wires and introducer sheaths into any artery or vein of the human body.

Thus an object of this invention is to place a guide wire and/or introducer sheath into a blood vessel while preventing the free release of blood.

Another object of this invention is to sense when an arterial access device has its distal opening properly placed within an artery by observing the pulsatile motion of the blood within a pressure tight transparent portion of the access device.

Still another object of this invention is to sense proper positioning of the distal opening of the arterial access device by observing the pulsatile motion of a diaphragm.

Still another object of the invention is to observe the pulsatile motion of the blood in a small diameter lumen so that the linear displacement between diastolic and systolic blood pressure is maximized.

Still another object of this invention is to provide an optical magnification means for the small diameter lumen through which the blood moves back and forth so that the blood's motion is more readily observed.

Still another object of this invention is to assemble as a single package in the form of a kit all items required for accessing both the femoral artery and the femoral vein for the introduction of introducer sheaths into those blood vessels.

BRIEF DESCRIPTION OF THE DRAWINGS

FIG. 4 is a longitudinal cross section at 4—4 of FIG. 6 showing a blood containment vascular access device that uses a sharpened distal end to eliminate the need for a stylet needle.

FIG. 5 is a partial cross section at 5—5 of FIG. of the blood containment vascular access device of FIG. 4 showing a guide wire partially advanced through the device's central lumen.

FIG. 6 is a transverse cross section of the device taken through section 6—6 of FIG. 5.

FIG. 7 is a plan view of the valve placed inside the end cap of FIGS. 4 and 5.

DETAILED DESCRIPTION OF THE INVENTION

Figure 1:
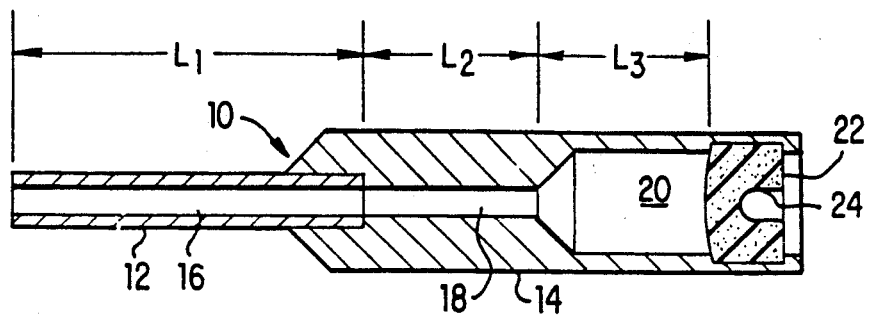
FIG. 1 is a longitudinal cross section of a blood containment arterial access device that allows the use of visual observation of pulsatile blood to determine that the device is properly placed within an artery.

FIG. 1 is a longitudinal cross section of a blood containment arterial access device 10 having a distal tube 12 onto which is molded or bonded a transparent viewing cylinder 14. The tube 12 has a lumen 16 which continues into the lumen 18 of the cylinder 14. The lumen 18 terminates in a chamber 20 which is sealed at the proximal end of the cylinder 14 by a soft elastomer septum 22 which has an entry hole 24 at its center.

Figure 2:
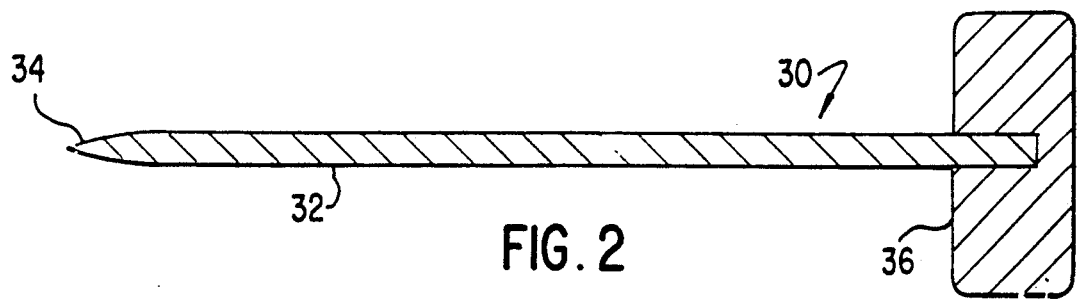
FIG. 2 is a longitudinal cross section of the stylet needle that is used with the embodiments of FIGS. 1 and 3.

The lumens 16 and 18 have an inside diameter which allows a sliding fit with the needle stylet 30 shown in FIG. 2. In use, the stylet 30 would be passed through the entry hole 24 and advanced until its distal point 34 lies distal to the distal end of the tube 12 and its handle 36 is in contact with the proximal end of the viewing cylinder 14. When assembled in this manner, the stylet 30 would penetrate the skin above the femoral artery at the groin and the assembly of the access device 10 and the stylet 30 would then be advanced until their distal ends penetrated through the femoral artery. The stylet 30 would then be removed and the device 10 pulled back until the distal end of the tube 12 entered the lumen of the femoral artery. The blood would then rush through the lumen 16 and into the viewing lumen 18. Once blood enters the distal end of the lumen 16, the volumes of the lumens 16 and 18 and the chamber 20 form a closed, pressure tight volume. The pressure of the blood entering this volume will compress the air in this closed volume until the air pressure is equal to the blood pressure. When the pressure in this closed volume reaches systolic pressure, no additional blood will enter the volume and all the blood will be contained within the blood containment arterial access device 10. As the blood pressure varies between systolic and diastolic, blood will flow into and out of the volume with the pressurized trapped air contracting and expanding accordingly.

Figure 8:
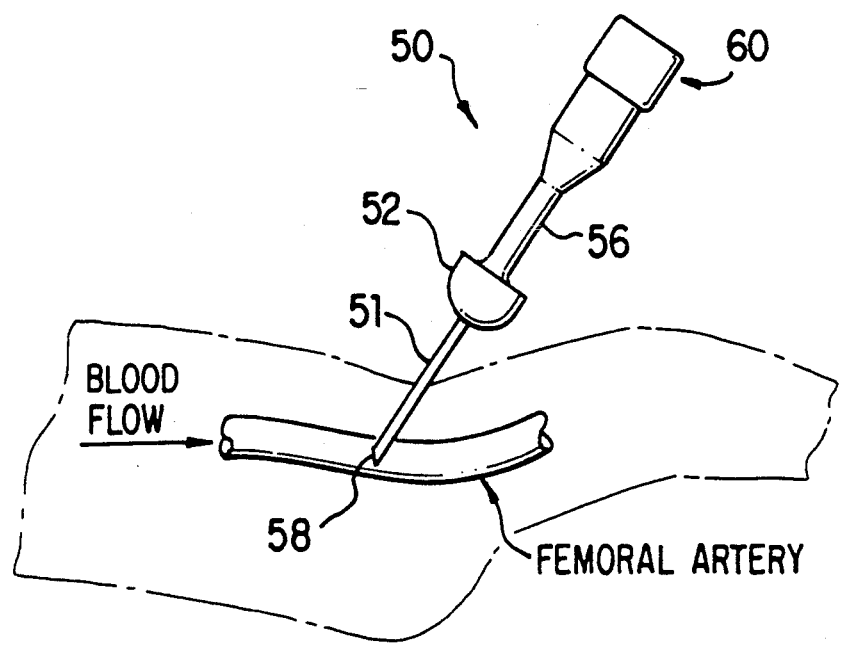
FIG. 8 shows the access device of FIGS. 4 and 5 being inserted into a femoral artery.
Figure 11:
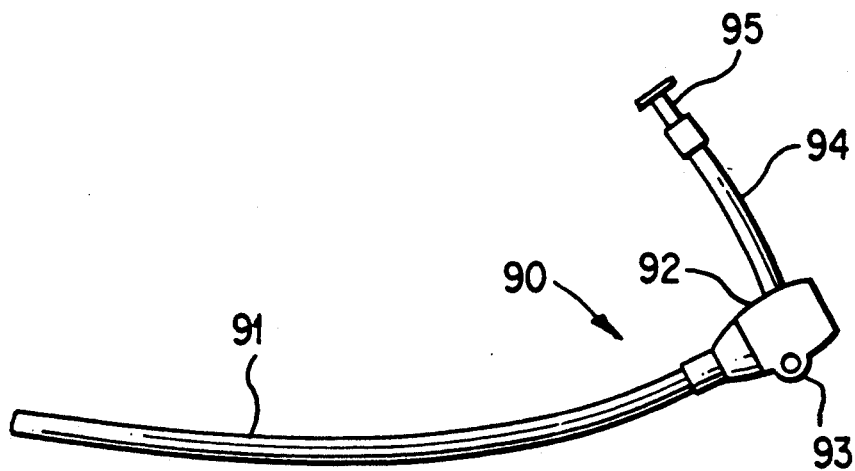

If, as seen in FIG. 11 the dimension L1=2.0 inches, L2=L3=1.0 inches and if the diameter of the lumens 16 and 18 is 0.040 inches and the diameter of the chamber 20 is 0.200 inches then at a normal diastolic pressure of 80 Mm Hg the blood would just reach slightly into the viewing lumen 18. At a normal systolic pressure of 140 mm Hg, the blood would just squirt into the chamber 20. By tilting the access device 10 at approximately a 45 degree angle (as seen in FIG. 8) and viewing it from above, the physician can watch the blood pulse into and out of the chamber 20 confirming that the distal end of the tube 12 is within the lumen of the femoral artery. Thus the goal of this invention which is the assurance of proper placement of the distal end of the tube 12 within the femoral (or any other accessed) artery while disallowing the uncontrolled release of blood has been accomplished.

It should be understood that the purpose of having a smaller diameter of the lumen 18 and a larger diameter for the volume 20 is so that, even at comparatively low diastolic pressures, blood will appear in the lumen 18 while the total length L2+L3 is minimized. If the diameter of volume 20, were the same as the much smaller diameter of the lumen 18, then the total length of the access device 10 would have to be considerably longer making it more awkward to handle. Furthermore it should be pointed out that the lumen 18 has a minimum diameter that will just pass the guide wire. This minimum diameter design provides a maximum linear displacement of the blood as it pulses within the lumen 18 between diastolic and systolic pressures thus providing optimum visualization.

Still further, the viewing cylinder 14 is thick-walled and has a convex outer surface thereby providing an optically magnified image of the small diameter lumen 18 which enhances the observability of the blood that moves back and forth in a pulsatile fashion in the lumen 18.

After the correct placement has been ascertained by observation of the blood pulsating within the lumen 18, a guide wire can be inserted through the entry hole 24, and then it will pass through the central incision made in the septum 22 by the needle 32 of the stylet 30. The guide wire is then advanced through the lumens 18 and 16 and finally the guide wire's distal end will enter the femoral artery. The access device 10 can then be removed from the body while leaving the guide wire remaining in place in the arterial lumen. The typical guide wire for this application would have a diameter of 0.038 inches.

The tube 12 and the stylet needle 32 would typically be made from Type 304 stainless steel. The viewing cylinder 14 would typically be made from a transparent plastic such as Lucite or Lexan. The septum 22 would be made from a low durometer latex or silicone rubber such as used for the top of bottles for injectable drugs. The handle 36 of the stylet 30 could be molded from any moldable plastic such as PVC.

Figure 3:
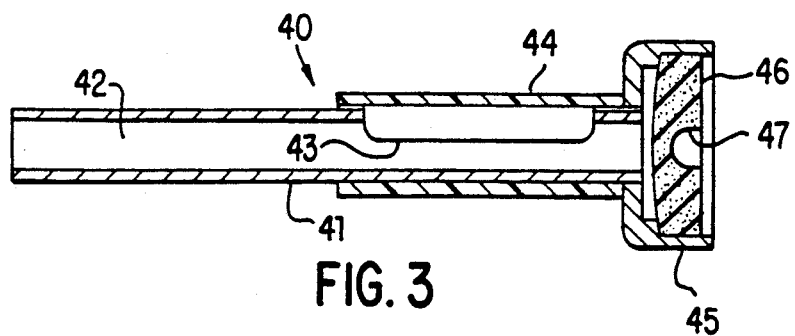
FIG. 3 is a longitudinal cross section of another embodiment of a blood containment arterial access device which uses a thin diaphragm to allow detection of proper placement in an artery.

FIG. 3 shows an alternative embodiment of the present invention. This pressure sensing arterial access device 40 has a tube 41 which has an interior lumen 42 and a cut out window 43. Wrapped around the window 43 is a thin-walled elastic diaphragm 44. At the proximal end of the tube 41 is a septum holder 45 into which is placed a soft elastomer septum 46 having a central hole 47.

The method for using this device is as follows:
(1) The stylet needle 30 is placed through the septum 46 until its sharpened end 34 extends beyond the distal end of the tube 41.
(2) This assembly penetrates through the femoral artery at the groin and the stylet 30 is removed.
(3) The device 40 is then pulled back until the distal end of the lumen 42 lies within the lumen of the femoral artery.
(4) The pressurized blood rushes into the lumen 42 thus raising the pressure in the volume enclosed by lumen 42 to the pressure of the blood and causing pulsation of the diaphragm 44.

This embodiment differs from that shown in FIG. 1 in that instead of visual observation of the confined blood, the physician places a finger over the diaphragm 44 while pulling back on the device 40 until a pulse is felt on the diaphragm indicating that the pressure in the lumen 42 is changing between diastolic and systolic blood pressure. Alternatively a pulsing movement of the diaphragm could be visually observed. After correct positioning is noted, a guide wire can be passed through the septum 46 through the lumen 42 and into the femoral artery.

Both the embodiments of FIGS. I and 3 confine the blood to a very small, comparatively rigid, enclosed volume which has an elastomer septum at the device's proximal end which septum is designed to be penetrated first by a needle stylet and then by a guide wire.

FIGS. 4 to 7 inclusive show another embodiment of the present invention in the form of an arterial access device 50 that is designed to be used without a stylet needle. FIGS. 4 and 5 show the access device 50 with a distal metal tube 51 which has a sharpened distal tip 53. The purpose of the sharpened distal tip 53 is to penetrate through the tissue at the groin and penetrate the proximal wall of the femoral artery but not the distal wall so that the distal opening 58 is placed inside the arterial lumen. The distal opening 58 is the terminus of the lumen 54 (see FIG. 4) which is in fluid communication with the viewing lumen 55 of the transparent viewing section 56 which lumen 55 is in fluid communication with the proximal chamber 57 of the viewing section 56.

Luer type threads 49 are formed at the proximal end of the viewing section 56 in order mate with a separate Luer end cap 60. The end cap 60 has a generally cylindrical body 61 which has a tapered proximal access hole 63 which leads into a central lumen 62 through which a guide wire can be passed. The outer perimeter of an elastomer valve 68 is adhesively joined to the interior distal surface of the end cap 60. The valve 68 has a valve poppet 64 (see FIGS. 4, 5 and 7) which has a cylindrical extension 65 into the lumen 62. The valve 68 including the extension 65, forms an air-tight seal at the proximal end of the chamber 57. After the access device 50 has been placed so that its distal opening 58 is within the arterial lumen, as shown in FIG. 8, the blood will rush into the lumens 54 and 55 and the air in the chamber 57 will undergo pulsatile compression. At diastolic pressure, the blood extends just proximal to the proximal end of the lumen 54; i.e., into the distal end of the lumen 55. At normal systolic pressures the column of blood extends into the proximal end of the (approximately one inch long) lumen 55, and at higher systolic blood pressures some blood will enter the conically shaped distal end of the chamber 57. When the physician see that the blood is pulsing back and forth sharply within the lumen 55, he knows that the distal opening 58 is well placed within the arterial lumen. Then, as seen in FIG. 5, a guide wire 70 can be pushed through the conical opening 63 of the end cap 60, and as the guide wire 70 is further advanced, it forces the valve Poppet 64 to open. As seen in FIG. 7, the valve poppet generally bends around the dotted line 67. The guide wire 70 is then advanced further through the chamber 57 and into the lumens 55 and 54, and then out the distal opening 58 and into the arterial lumen. The access device 50 including the end cap 60 is then pulled back and out of the body while leaving the guide wire 70 in place.

An important feature of this invention is an improved means for the physician to conveniently hold the access device 50 so that it can be readily pushed through as much as through 2.5 inches of the patient's skin and tissue so as to place the opening 58 into the lumen of the femoral artery. This can require several pounds of force. Specifically, FIGS. 5 and 6 show the flat side surface 59A which can be comfortably grasped by the physician between the thumb and forefinger. The front surface 59B of the bulbous distal end 52 of the viewing section 56 allows the physician to readily provide a high degree of forward thrust without relying on frictional forces of the thumb and forefinger against the side surfaces 59A. This design is clearly superior to a simple, straight steel needle which is in current use which is much more difficult to grasp for thrusting through the skin and tissue.

It should also be noted that the flat surfaces 59A have a specific orientation relative to the plane of the opening 58. Specifically, when the surfaces 59A are vertical and the tube 51 is tilted downward at about 45 degrees relative to the longitudinal axis of the femoral artery (see FIG. 8), and where the element line 52 touches the device 50 in FIGS. 4 and 8 and is upward facing toward the physician, then the plane of the opening 58 will be generally perpendicular to the longitudinal axis of the femoral artery. This orientation (as seen in FIG. 8) provides the strongest pulsing of the blood into the viewing section 56 and is also the best orientation for placing the guide wire into the arterial lumen.

It should also be noted that the surface 59C in FIG. 6 is convex, and there is a thick wall, thereby providing optical magnification of the small diameter lumen 55 so as to enhance the ability of the physician to readily observe the pulsatile motion of the blood within the lumen 55.

The materials for the embodiment of the invention shown in FIGS. 4, 5, 6 and 7 would be of the same type as those used for the embodiment shown in FIG. 1.

When performing percutaneous transluminal coronary angioplasty (PTCA) with a balloon catheter, interventional cardiologists typically place at the groin one sheath into the femoral artery (through which the balloon angioplasty catheter is inserted) and the second sheath is placed to the femoral vein for injecting medications and/or making pressure measurements. The embodiment shown in FIGS. 4 and 5 can be used for placing these two sheaths, one in the vein and the other in the artery. The method for placing these sheaths is as follows:

(1) Using the embodiment shown in FIGS. 4 and 5, after first cleaning the skin surface with an antibacterial solution and then making a small cut at that site with a scalpel, the sharpened point 53 is pushed through the tissue at the groin over the site of the femoral artery.

(2) The access device 50 is then pushed forward until the opening 58 of the tube 51 lies within the lumen of the femoral artery.

(3) Arterial blood will then rush through the opening 58, into the lumens 54 and 55 and, at higher systolic pressure, into the chamber 57.

(4) The blood under arterial pressure will then be able to be seen (with optical magnification) pulsating within the lumen 55 and occasionally spurting into the chamber 57. The physician then has a clear indication that the tube 51 has its distal opening 58 placed properly in the lumen of the femoral artery.

(5) When the proper positioning of the access device 50 has been ascertained, a guide wire 70 is inserted through the lumen 62 of the end cap 60 as shown in FIG. 5. The guide wire 70 would force the valve poppet 65 to open and then the guide wire 70 would be advanced through the lumens 55 and 54, through the opening 58 and into the arterial lumen.

(6) The device 50 can then be pulled out the artery while the guide wire 70 remains in place in the arterial lumen.

(7) An introducer sheath would then be inserted over the guide wire into the femoral artery.

(8) The guide wire and dilator portion of the introducer sheath would then be removed leaving the sheath in place.

(9) The end cap 60 would then be removed from the access device 50 and a syringe would be joined to the proximal end of the device 50 with the syringe's plunger being fully advanced.

(10) The sharpened point 53 would then be pushed into the femoral vein while pulling back on the plunger of the syringe so as to create a partial vacuum inside the device 50.

(11) When the blood can be seen to reach the chamber 57, the syringe is removed and a guide wire is advanced through the device 50 and into the lumen of the vein.

(12) The device 50 is then pulled out of the body while leaving the guide wire in place.

(13) An introducer sheath is then advanced over the guide wire and into the lumen of the vein.

(14) The sheath's dilator and guide wire are then removed leaving the sheath in place in the vein.

To accomplish the placement of one sheath in the femoral artery and a second sheath in a vein, it would be convenient for the interventional cardiologist to have the following items in the form a single package or kit:

(1) An access device 50.
(2) End cap 60.

(3) One or two guide wires 70.
Additionally it might be advantageous to include:
(4) A syringe, and
(5) A disposable scalpel.

Figure 9:
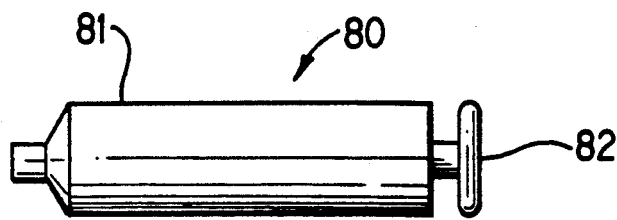
Figure 10:
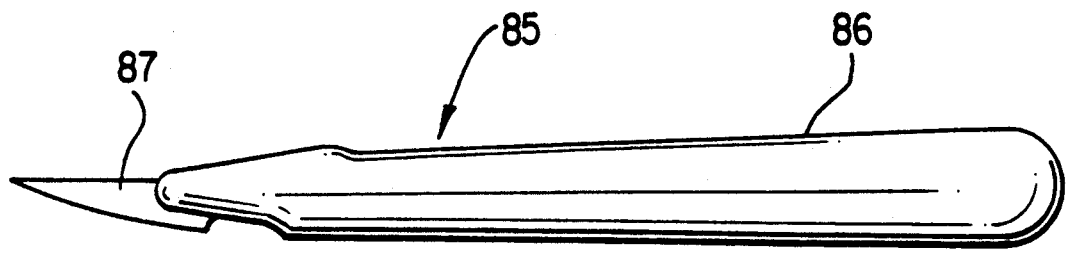

Additionally one might wish to include two introducer sheaths into the kit. FIGS. 9, 10 and 11 illustrate respectively typical designs for a syringe 80, having body 81 and plunger 82; a scalpel 85 having plastic handle 86 and blade 87, and sheath 90 having a cylindrical body 91, hemostatic valve fitting 92 with a suture ring 93, and a side arm 94, and having a Luer fitting 95. Such a kit would be in the form of a single, sterilized package. Having all these items in a single package would make the Placement Of the two sheaths required for PTCA quicker, easier and more convenient.

It should be understood that the design of FIGS. 4 and 5 could be used with the stylet needle design Of FIG. 1. If this were the case, the valve 68 would preferably have a single central hole through which the stylet could pass while maintaining a pressure seal. After the stylet tip 34 (Of FIG. 2) penetrates through both arterial wails, the stylet 40 would be pulled back until the tip 34 lies within the chamber 57. The access device 50 would then be pulled back until Pulsatile blood appeared in the lumen 55. The stylet would then be removed and a guide wire would quickly be inserted through the cap 60 and passed forward into the arterial lumen.

It should also be understood that the embodiments of FIGS. 1 and 3 could be used with a sharpened chisel-like tip as illustrated in FIGS. 4 and 5 without the use of a stylet. Each of these designs is capable of accomplishing the goal of the present invention which is to provide a means for inserting a guide wire into an artery and/or vein while providing blood containment. Still further, all of the designs described herein are applicable to any percutaneous vascular access and are not limited to groin access of the femoral artery. Furthermore these designs could be used for percutaneously or intraoperably accessing human organs such as the spinal column or bladder for acquiring other fluids such as the cerebrospinal fluid (CSF), urine, etc.

Various other modifications, adaptations and alternative designs are of course Possible in light of the above teachings. Therefore it should be understood at this time that within the scope of the appended claims, the invention may be practiced otherwise than as specifically described herein.

What is claimed is:
1. A vascular access device comprising:
a hollow thin-walled metal tube having distal and proximal ends, and having an opening at the tube's distal end, and further having a lumen extending freely from the opening at the tube's distal end to the tube's proximal end; and,
a transparent viewing section having distal and proximal ends, the distal end of the viewing section forming a first pressure tight seal with the metal tube's proximal end and having an interior lumen which is in fluid communication with the lumen of the metal tube, guide wire access means forming a portion of said transparent viewing section and having a second pressure tight seal at the viewing section's proximal end thereby forming an enclosed fixed volume non-venting chamber within the viewing section so as to contain any blood that enters into the opening at the tube's distal end, the blood being contained within the metal tube and viewing section, and the guide wire access means being adapted to allow passage of a guide wire through the viewing section and into the metal tube, the guide wire access means being further adapted to provide said second pressure tight seal to prevent free release of the blood prior to insertion of the guide wire through the guide wire access means.

2. The access device of claim 1 wherein the viewing section has a distal lumen having a first, smaller diameter within which the reciprocating pulsatile motion of a column of arterial blood can be observed and a second, larger diameter proximal lumen which forms a proximal chamber which is sealed at its proximal end by the pressure tight seal formed within the guide wire access means, said proximal chamber having air trapped within it which becomes pressurized alternatively at systolic and diastolic pressure when the opening at the distal end of the metal tube is placed within an arterial lumen.

3. A vascular access device comprising:
a hollow thin-walled metal tube having distal and proximal ends and having a central lumen extending freely from the tube's distal end to the tube's proximal end and further having an opening at the tube's distal end;
a transparent viewing section having distal and proximal ends, the distal end of said viewing section forming a pressure tight seal with the metal tube's proximal end, the viewing section having a first, smaller diameter elongated distal lumen which is in fluid communication with the metal tube's lumen, said viewing section also having a second, larger proximal diameter lumen forming a proximal chamber extending into the viewing cylinder's first lumen, said second lumen being in fluid communication with said first lumen; and,
a separate end cap removeably connected to the viewing cylinder's proximal end, the end cap incorporating an air-tight eleastomer valve within a central lumen of said end cap which central lumen is designed for the passage of a guide wire, which guide wire is adapted to pass through the elastomer valve as the guide wire is advanced through the end cap and into the viewing section.

4. The vascular access device of claim 3 wherein the viewing section has a flat-walled section whose distal extremity is joined to a bulbous section which cooperates with the flat-walled section to form a region which is adapted to allow the force of the thumb and forefinger to be conveniently applied for exerting forward thrust on the vascular access device for the purpose of readily pushing the distal end of the thin-walled metal tube through body tissue so as to place the opening at the tube's distal end into the lumen of an artery.

5. The vascular access means of claim 4 wherein the flat-walled section has a known and controlled orientation relative to the plane of the opening at the metal tube's distal end so as to allow the physician to place the perpendicular to the plane of the tube's distal opening in generally the same direction as the longitudinal axis of the lumen of the blood vessel that is being accessed.

6. The vascular access device of claim 3 wherein the diameter of the smaller diameter lumen of the transparent viewing section is approximately the same diameter as the lumen of the metal tube.

7. The vascular access device of claim 3 wherein the transparent viewing section has a thick wall and has at least one outer surface which is convex in shape; the combination of the thick wall and the convex shape resulting in optical magnification of the small diameter lumen so that a reciprocating pulsating column of arterial blood within the small diameter lumen is more readily observable.

8. The vascular access device of claim 3 wherein the thin-walled metal tube has a sharpened tip at its distal end.

9. The vascular access device of claim 3 wherein the thin-walled metal tube is cut off square at its distal end.

10. The vascular access device of claim 9 further comprising a stylet having a sharpened distal end which is adapted to pass through the elastomer valve, the viewing cylinder and the thin-walled metal tube with the sharpened distal end protruding beyond the distal end of the metal tube.

11. A vascular access device insertable into a blood vessel for allowing observation of a pulsating column of blood therein and providing insertion therethrough of a medical instrument into said blood vessel, comprising:
  (a) a thin-walled metal tube having a lumen passing therethrough from a distal end to a proximal end thereof;
  (b) a transparent viewing member having first and second sections in fluid communication with each other, said first section of said transparent viewing member having distal and proximal ends and being secured to said thin-walled metal tube and having a first section lumen extending therethrough in fluid communication with said lumen of said thin-walled metal tube, said second section of said transparent viewing member defining a pressure responsive chamber, said pressure responsive chamber forming a non-venting enclosure for containing pressurized air whereby said air pressure varies between systolic and diastolic pressures of said pulsating column of blood; and,
  (c) an elastomer valve that allows insertion of said medical instrument into said pressure responsive chamber, said pressure responsive chamber having a proximal end section and a distal end section, said elastomer valve being secured to said proximal end section of said pressure responsive chamber in fluid tight relation therewith for preventing egress of said pressurized air contained within said pressure responsive chamber prior to insertion therethrough of said medical instrument.

12. The vascular access device as recited in claim 11 wherein said pressure responsive chamber has a cross-sectional area greater than a cross-sectional area of said first section lumen, said pulsating column of blood being observable in said first section lumen.

13. The vascular access device of claim 11 wherein the diameter of said first section lumen is approximately the same diameter as said lumen of said metal tube.

14. The vascular access device of claim 11 wherein the respective volumes of said lumen of said metal tube, said first section lumen and said pressure responsive chamber are each adapted relative to each other such that said column of blood appears near the distal end of said first section lumen at typical diastolic blood pressures of a human being and near the proximal end of said first section lumen at typical systolic blood pressures of a human being.

15. The vascular access device of claim 11 wherein said elastomer valve is an elastomer septum.

16. The vascular access device as recited in claim 11 wherein said elastomer valve is a poppet type valve member.

17. The vascular access device as recited in claim 11 including an end cap member releasably secured to said transparent viewing member's second section, which end cap includes said elastomer valve.

18. The vascular access device as recited in claim 17 wherein said end cap member includes an end cap central lumen formed therethrough for passage of said medical instrument.

19. The vascular access device as recited in claim 11 wherein said medical instrument is a guide wire.

20. The vascular access device as recited in claim 11 wherein said medical instrument is a stylet having a sharpened point at its distal end.

21. A collection of devices for accessing both the femoral artery and the femoral vein in order to place sheaths or guide wires into each of these blood vessels, the collection of devices being in the form of a single package or kit consisting of;
  (1) a vascular access device having distal and proximal ends, an opening at its distal end and a fixed volume interior chamber in the form of a transparent viewing section which has a central lumen and being capable of determining that the opening at its distal end has been properly situated within the lumen of an artery by observation of a reciprocating pulsatile column of arterial blood within the central lumen of the transparent viewing section of the vascular device;
  (2) an end cap that is capable of being removeably connected to the proximal end of the vascular device the end cap forming a pressure tight seal and an access means for a guide wire; and,
  (3) a guide wire or sheath for insertion into the lumen of the femoral vein or the femoral artery.

22. The collection of devices of claim 21 further consisting of a hypodermic syringe whose distal end is adapted to be removeably connected to the proximal end of the vascular access device when the end cap is removed.

23. The collection of devices of claim 21 further consisting of a scalpel.

24. The collection of devices of claim 21 further consisting of one or two introducer sheaths that are adapted to be advanced over the inserted guide wires.

* * * * *